(12) United States Patent
Sumetsky

(10) Patent No.: US 8,368,899 B2
(45) Date of Patent: Feb. 5, 2013

(54) COILED EVANESCENT OPTICAL SENSOR

(75) Inventor: Mikhail Sumetsky, Bridgewater, NJ (US)

(73) Assignee: OFS Fitel, LLC, Norcross, GA (US)

( * ) Notice: Subject to any disclaimer, the term of this patent is extended or adjusted under 35 U.S.C. 154(b) by 274 days.

(21) Appl. No.: 12/853,710

(22) Filed: Aug. 10, 2010

(65) Prior Publication Data

US 2011/0043818 A1 Feb. 24, 2011

Related U.S. Application Data

(60) Provisional application No. 61/234,834, filed on Aug. 18, 2009.

(51) Int. Cl.
*G01B 9/02* (2006.01)
(52) U.S. Cl. ........................................ 356/477
(58) Field of Classification Search ................. None
See application file for complete search history.

(56) References Cited

U.S. PATENT DOCUMENTS

| | | | |
|---|---|---|---|
| 4,456,377 A | 6/1984 | Shaw et al. | |
| 4,787,741 A | 11/1988 | Udd et al. | |
| 5,004,914 A | 4/1991 | Vali et al. | |
| 6,040,908 A | 3/2000 | Rahn et al. | |
| 6,862,386 B2 | 3/2005 | Corio et al. | |
| 6,887,359 B2 | 5/2005 | Ruggiero | |
| 7,218,803 B1 | 5/2007 | Sumetsky | |
| 7,266,259 B1 | 9/2007 | Sumetsky | |
| 7,477,806 B2 | 1/2009 | Williams | |
| 7,957,623 B2 * | 6/2011 | Panarello et al. | 385/134 |
| 2006/0170931 A1 | 8/2006 | Guo et al. | |
| 2008/0002186 A1 * | 1/2008 | Masterson et al. | 356/73.1 |
| 2008/0095495 A1 | 4/2008 | Taverner et al. | |
| 2009/0010588 A1 | 1/2009 | Sumetsky | |
| 2009/0059233 A1 | 3/2009 | Sumetsky | |
| 2009/0080470 A1 | 3/2009 | Ramachandran et al. | |

OTHER PUBLICATIONS

Sumetsky et al., "The Microfiber Loop Resonator: Theory, Experiment and Application", Journal of Lightwave Techonology, vol. 24, No. 1, Jan. 2006.
Cao et al., "Optical Fiber-based Evanescent Ammonia Sensor", Sensors and Actuators, B110 (2005), pp. 252-259.
Yao et al., "Low Bend Loss in Tightly-Bent Fibers Through Adiabatic Bend Transitions", Feb. 16, 2009/vol. 17, No. 4/Optics Express.
Xu et al., "Optical Microfiber Coil Resonator Refractometric Sensor", Jun. 11, 2007/ vol. 15, No. 12/ Optics Express.
Xu et al., "An Embedded Optical Nanowire Loop Resonator Refractometric Sensor", Jan. 21, 2008/vol. 16, No. 2/ Optics Express.
Sumetsky et al., "Demonstration of a Microfiber Loop Optical Resonator", 2005 Optical Society of America.

(Continued)

*Primary Examiner* — Tu Nguyen
(74) *Attorney, Agent, or Firm* — Wendy W. Koba, Esq.

(57) ABSTRACT

An evanescent optical sensor is formed as a coil of either optical fiber or microfiber. By coiling the fiber/microfiber, the overall size of the sensor is significantly reduced when compared to "straight path" fiber sensors, yet exhibits a similar degree of sensitivity. An optical signal is coupled into a fiber coil that has been immersed in an ambient to be analyzed. The use of a coil configuration results in creating a plurality of whispering gallery modes (WGMs) that will propagate along the coil by reflecting from the surface of the curved fiber/microfiber forming the coil. The interference between these modes will be modified as a function of the properties of the ambient environment. Environmental changes cause variations in the optical length of the coil as "seen" by the various modes, and the interference of the modes is analyzed by studying the transmission spectrum at the output of the coil.

16 Claims, 4 Drawing Sheets

OTHER PUBLICATIONS

Sumetsky, "Optical Microfibers: Fundamentals and Applications", 2006 Optical Society of America.

Sumetsky, "Optical Microfiber Coil Delay Line", Apr. 27, 2009/vol. 17, No. 9/Optics Express.

Sumetsky, "Uniform Coil Optical Resonator and Waveguide: Transmission Spectrum, Eigenmodes, and Dispersion Relation", May 30, 2005/vol. 13, No. 11/Optics Express.

Xu et al., "Conical and Bi-Conical High-Q Optical Nanofiber Microcoil Resonator", Optoelectronics Research Centre, University of Southampton, Southampton, United Kingdom.

Annovazzi-Lodi et al., "Coiled-Fiber Sensor for Vectorial Measurement of Magnetic Field", Journal of Lightwave Technology, vol. 10, No. 12, Dec. 1992.

* cited by examiner

125 μm FIBER

125 μm FIBER

10 μm MICROFIBER 0.9 μm MICROFIBER

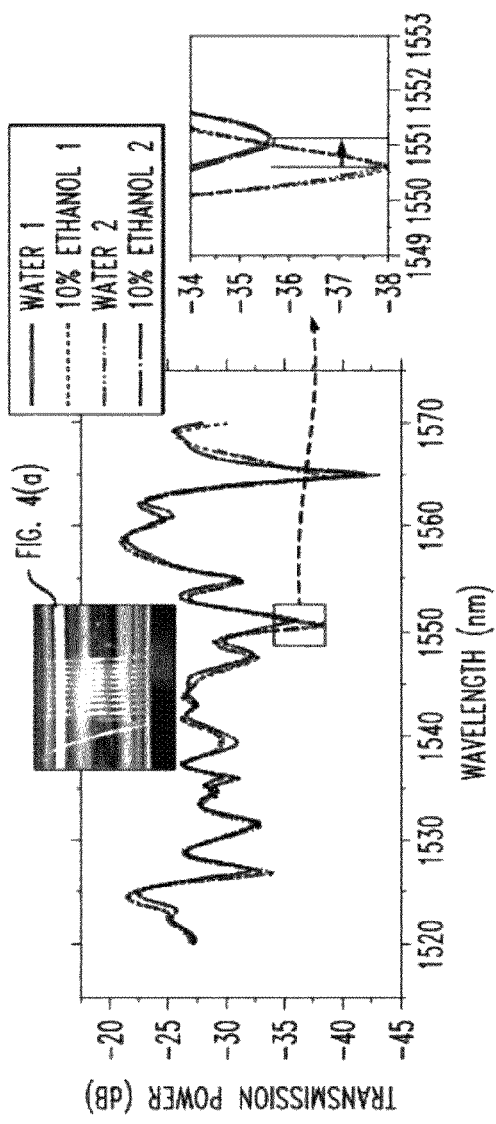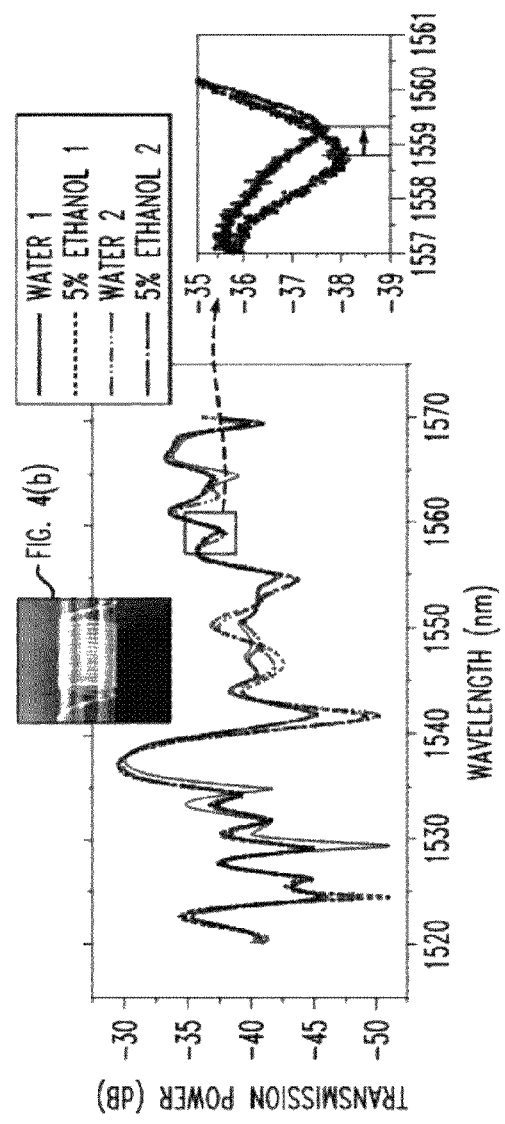
FIG. 6(a)
FIG. 6(b)

COILED EVANESCENT OPTICAL SENSOR

CROSS-REFERENCE TO RELATED APPLICATIONS

This application claims the benefit of US Provisional Application No. 61/234,834, filed Aug. 18, 2009 and herein incorporated by reference.

TECHNICAL FIELD

The present invention relates to an evanescent optical sensor and, more particularly, to an evanescent optical sensor in the form of a fiber coil.

BACKGROUND OF THE INVENTION

Optical waveguides and, in particular, optical fibers, are often used for sensing changes in an ambient medium. Optical sensors have been used to measure changes in various parameters such as temperature, pressure, sound, refractive index and the like. In many cases, these changes are detected by monitoring the transmission (or reflection) spectrum of light as it propagates along an optical waveguide disposed within the ambient. Some optical sensors function as evanescent sensors based on the detection of changes in light propagating through an optical waveguide due to the optical mode that evanescently penetrates into the surrounding ambient.

Indeed, evanescent wave absorption is an effective technique for performing various types of environmental sensing. When a beam of light propagates along an optical fiber, the electromagnetic field does not abruptly fall to zero at the core/cladding interface. Instead, the overlap of an incoming beam and the internally reflected beam leads to a field that penetrates into the medium adjacent to the core region of the fiber. This electromagnetic field, which tails into the adjacent medium, is defined as the "evanescent field".

In order to enhance the response of the transmission (or reflection) spectrum to variations of ambient medium parameters, an optical sensor is typically configured as a Mach-Zehnder interferometer (MZI) having at least two separate arms along which an optical signal will propagate. At a given wavelength $\lambda$, the output power of an N-arm MZI is determined by the following equation:

$$P = \left| \sum_{n=1}^{N} A_n \exp(iL_n\beta_n) \right|^2,$$

where $L_n$ is defined as the length of waveguide n and $A_n$ and $\beta_n$ are the amplitude and propagation constants of the particular optical signal propagating along waveguide n. In the simplified case where n=2 and each arm has the same length L, the above equation reduces to the following relation:

$$P = |A|^2 \{1 + \cos[L(\beta_1 - \beta_2)]\}.$$

In the analysis of an exemplary measured parameter q (where q may be, for example, temperature, refractive index, etc.), a variation in q causes variation in at least one of the propagation constants, say $\beta_1(q)$. From the above, it is clear that the sensitivity of the sensor is proportional to the following:

$$\left| \frac{\partial P}{\partial q} \right| = L|A\sin[L(\beta_1 - \beta_2)]| \left| \frac{\delta \beta_1}{\delta q} \right|.$$

Thus, it is shown that the sensitivity grows proportionally to the length L of the MZI arm. For this reason, it is desirable to make the interferometer arm as long as possible. On the other hand, increasing the length L results in increasing the overall physical size of the sensor. The latter is undesirable for at least two reasons. First, this causes spatial delocalization of the measurement since the ambient may change over the length of the interferometer arm. Second, many applications require the use of a "miniature" sensor (for example, in a "lab on a chip" application).

It has previously been suggested to fabricate miniature MZI sensors based on photonic wires that are folded or spirally bent to be used as a planar photonic circuit. However, these devices are known to experience relatively high losses and cannot provide the degree of sensitivity required for many applications. Input/output coupling to/from these photonic wire devices is also problematic and introduces unwanted optical losses into the system.

Thus, a need remains in the art for a "miniature" optical sensor that exhibits the sensitivity generally associated with larger, multi-component arrangements.

SUMMARY OF THE INVENTION

The needs remaining in the prior art are addressed by the present invention, which relates to an evanescent optical sensor and, more particularly, to an evanescent optical sensor in the form of a fiber coil.

In accordance with the present invention, an evanescent optical sensor is formed as a coil of either optical fiber or microfiber. By coiling the fiber/microfiber, the size of the sensor is significantly reduced when compared to "straight path" fiber sensors, yet exhibits a similar degree of sensitivity. For example, a prior art sensor formed of a section of optical fiber having a length of 15 cm can now be formed as coil of dimensions 3 mm×3 mm×4 mm.

In operation, an optical signal is coupled into a coil that has been immersed in an ambient to be analyzed. The use of a coil configuration results in creating a plurality of whispering gallery modes (WGMs) that will propagate along the coil by reflecting from the surface of the curved fiber/microfiber forming the coil. The interference between these modes (i.e., at least two modes) is modified as a function of the properties of the ambient environment within which the coil is immersed. That is, environmental changes cause variations in the optical length of the coil as "seen" by the various modes, with the interference between/among the modes analyzed by studying the transmission spectrum at the output of the coil.

It is an advantage of the compact nature of the coiled structure of the present invention that spatial delocalization of the measurement, associated with relatively "long" prior art sensors, is essentially eliminated.

Other and further advantages and aspects of the present invention will become apparent during the course of the following discussion and by reference to the accompanying drawings.

BRIEF DESCRIPTION OF THE DRAWINGS

Referring now to the drawings,

FIG. 3 represents numerical modeling associated with the coil of FIG. 1, where

FIGS. 6(a) and (b) show the transmission spectra of exemplary coiled microfiber evanescent optical sensors formed in accordance with the present invention.

DETAILED DESCRIPTION

An evanescent optical sensor useful for analyzing various parameters of the ambient environment (e.g., temperature, pressure, acoustic, refractive index, etc.) is formed from a coiled configuration of an optical fiber or microfiber. For the purposes of the present invention, the term "microfiber" is defined as a fiber with a diameter on the order of one micron (or less than/or on the order of the wavelength of an optical signal propagating through the fiber). It is contemplated that the coiled sensor of the present invention may be constructed of either conventional optical fiber (having a diameter on the order of ten to a hundred microns) or microfiber, where differences in sensitivity of various embodiments can be attributed, in part, to the selection of either fiber or microfiber.

Figure 1:
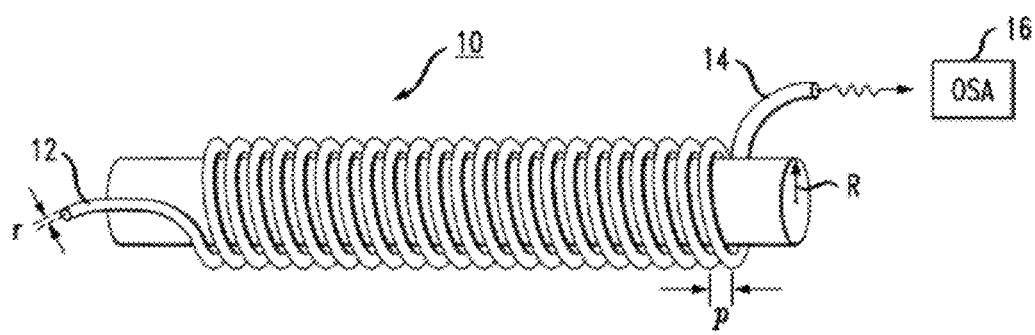
FIG. 1 is a depiction of an exemplary fiber coil useful as an evanescent optical sensor in accordance with the present invention.

FIG. 1 illustrates an exemplary coil 10 that may be used to form the evanescent optical sensor of the present invention. Coil 10 may be formed of either optical fiber or microfiber and is defined by parameters including but not limited to: the radius R of the coil, the length L of the coil, the pitch P (which is the spacing between adjacent turns of the coil), the radius r of the fiber forming the coil, and the refractive index profile of the fiber/microfiber. An input coupler 12, also formed of fiber, is used to introduce an optical signal into coil 10. Input coupler 12 functions as a mode converter to transfer a propagating fundamental mode optical signal into a plurality of optical signal modes, where in the case of a fiber coil, these modes take the form of whispering gallery modes (WGMs) that propagate along coil 10 by reflecting off the inner surface of the coiled fiber. An output coupler 14 is used to capture the signal exiting coil 10, where this signal is thereafter provided as an input to an optical spectrum analyzer 16 (or other appropriate device) to study the ambient-based changes to the spectrum (transmission or reflection) of the propagating optical signal based upon the presence of a plurality of propagating modes.

It is preferred that the radius of curvature R of the coil is gradually transitioned between infinity (within each coupler 12, 14) and the selected value as the signal is coupled into and out of the coil itself (that is, it is preferred that couplers 12 and 14 take the form of adiabatic couplers and mode converters). However, it is not necessary that output coupler 14 perform a mode conversion function. As compared to conventional "planar" optical sensors, the coiled configuration of the present invention creates a long optical path length (providing increased sensitivity) within a relatively compact area.

Figure 2:
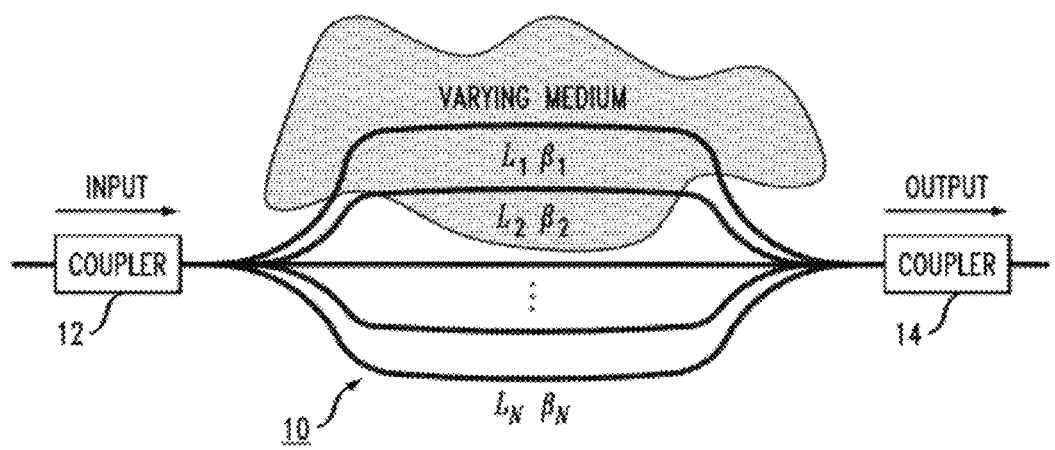
FIG. 2 is a simplified diagram of a multiple-arm MZI (representing the propagation of multiple modes) and its interaction with a "varying medium" ambient.

In operation, an incoming optical signal is propagating as a fundamental mode signal at the entrance of input optical coupler 12. Optical coupler 12 introduces the signal into coil 10, and functions as a mode converter so as to split the propagating optical signal into a plurality of modes, particularly in the form of whispering gallery modes (WGMs) that will thereafter propagate along coil 10, where at least two modes are required to be exited. The mode(s) nearer the outer surface of coil 10 will necessarily interact with a larger amount of the ambient, as shown in FIG. 2, which illustrates $L_1\beta_1$ and $L_2\beta_2$ as affected by the ambient. The ambient will affect the refractive index "seen" by the modes and thus affect the spectrum of the optical signal at the output of the coil. Output coupler 14 may also, in one embodiment, function as a mode converter to combine the multiple modes into an optical output signal that is thereafter applied as an input to an OSA 16. Alternatively, the multimode output signal may be directly coupled to OSA 16.

Figure 3A:
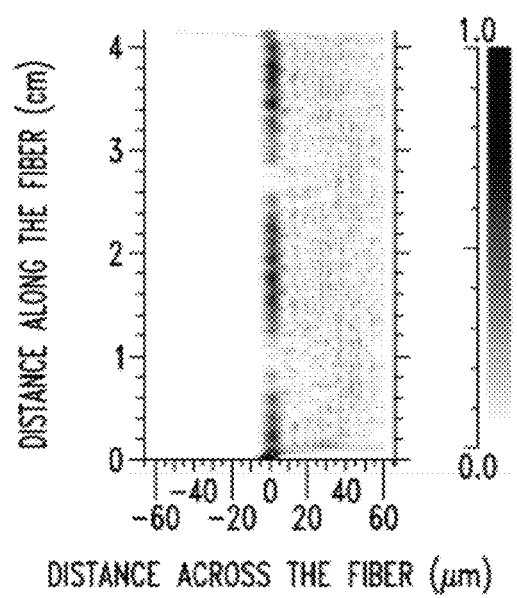
FIG. 3(a) depicts an exemplary field distribution along the length of the coil and FIG. 3(b) depicts an exemplary transmission power as a function of wavelength at the output of the coil of FIG. 1.
Figure 3B:
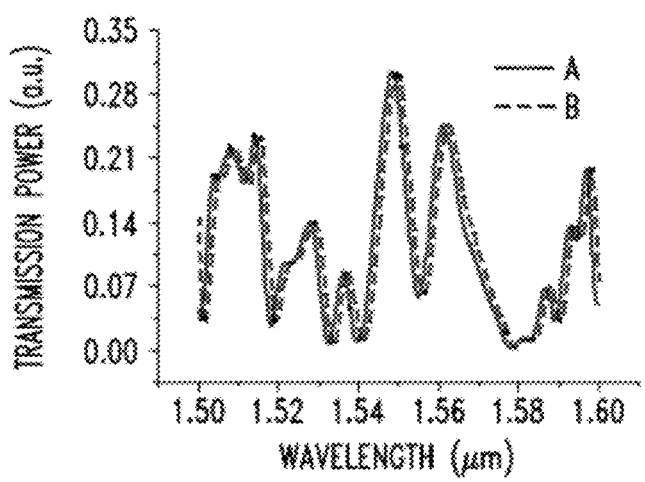
Figure 3C:
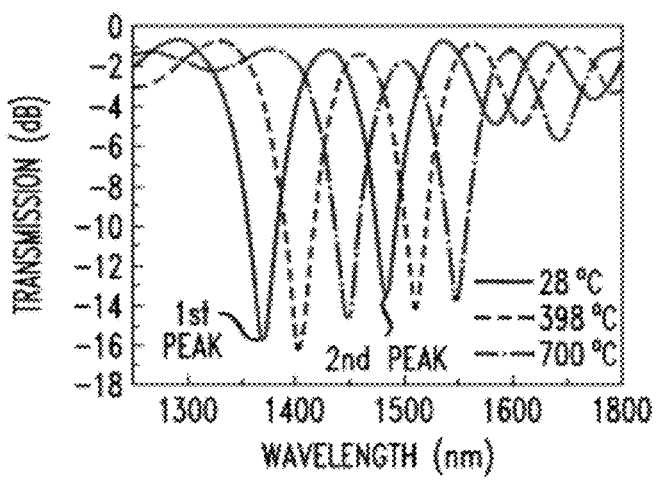
FIG. 3(c) is a prior art plot of transmission power associated with a conventional fiber loop temperature sensor, included for the sake of comparison.

FIGS. 3(a) and (b) illustrate the results of performing numerical modeling of coiled fiber sensor 10 of FIG. 1. For the modeling, coil 10 was presumed to be formed of standard single mode fiber (with a radius r of 62.5 µm). The coil itself was formed to have a radius R of 2.5 mm, and a coil length L of 4 cm was used. In accordance with the present invention, the sensitivity of coil 10 depends upon the refractive index of the ambient medium. At the intersection between input coupler 12 and coil 10, the fundamental mode of a propagating input signal is split into a plurality modes. The simulation used to create the plots of FIGS. 3(a) and (b) was performed by the beam propagation method (BPM). The field distribution along coil 10 is shown in FIG. 3(a). The transmission power as a function of wavelength is shown in FIG. 3(b). FIG. 3(c), included for comparison purposes, is a graph of transmission spectra for a prior art optical fiber loop sensor, used as a temperature sensor.

For the purposes of this analysis, the refractive index of the ambient medium surrounding coil 10 was set to the value of 1.000 for curve A and to 1.001 for curve B. It is seen that the characteristic oscillations of the transmission power are relatively frequent than those of the transmission associated with a prior art fiber loop sensor, as shown in FIG. 3(c). Also, the maximum slope of curve A is about forty times greater than the slope of the transmission spectra of FIG. 3(c). From a study of FIG. 3, therefore, it is found that variation of the refractive index of the ambient medium by 0.001 results in a spectrum shift on the order of approximately 1.2 nm, creating a shift in sensitivity on the order of 1200 nm/RIU (refractive index unit). As mentioned above, the sensitivity can be optimized by choosing the appropriate wavelength interval and by modifying the parameters of the coil itself (e.g., decreasing pitch, increasing the number of turns, etc.).

Figure 4A:
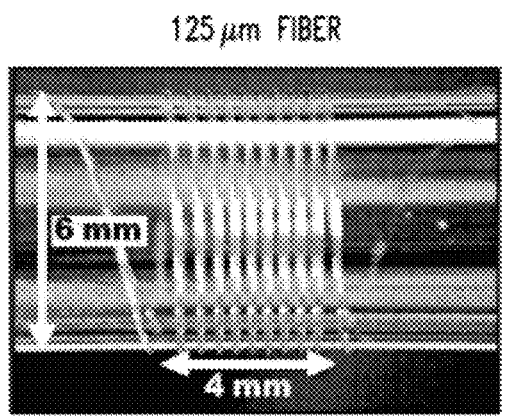
FIGS. 4(a) and (b) are photographs of exemplary coiled fiber evanescent optical sensors formed in accordance with the present invention.
Figure 4B:
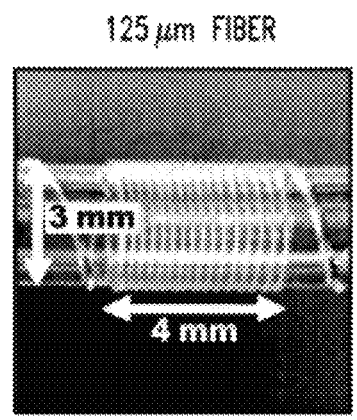

FIGS. 4(a) and (b) are digital camera pictures of exemplary coiled fiber sensors, where the coil of FIG. 4(a) is wound on a silica tube having a 6 mm outer diameter and the coil of FIG. 4(b) is wound on a silica tube having a 3 mm outer diameter. In both cases, standard optical fiber having a 62.5 micron radius was used to form a coil having al length L of 4 mm created. The coil of FIG. 4(a) has 11 turns, a pitch of 377 µm and comprises 207 mm of fiber. The overall size of this coil is 6 mm×6 mm×4 mm. The coil of FIG. 4(b) has 16 turns, a pitch of 245 μm and comprises a total of 151 mm of fiber, with an overall size of 3 mm×3 mm×4 mm.

The exemplary coiled fiber sensors of FIGS. 4(a) and (b) have been studied when used as evanescent refractometric sensors. In particular, the variation of transmission spectra for these coils was analyzed as the coils were alternately immersed in water and aqueous solutions of ethanol. The coil of FIG. 4(a) was first immersed in water (refractive index 1.3333), followed by immersion in a 10% ethanol bath (refractive index 1.339), then a second immersion in water, and finally a second immersion in a 10% ethanol bath. The coil of FIG. 4(b) was immersed in baths that varied between water and a 5% ethanol solution (refractive index 1.336).

Figure 5A:
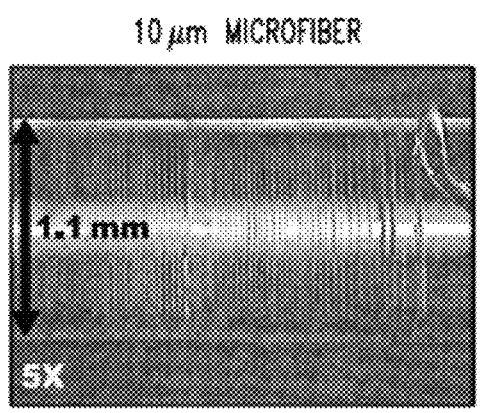
FIGS. 5(a) and (b) are diagrams of transmission power as a function of wavelength for the coiled fiber evanescent optical sensors of FIGS. 4(a) and (b), respectively.
Figure 5B:
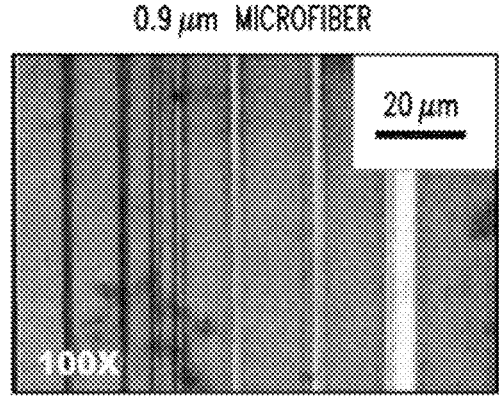

It was found that the coil as shown in FIG. 4(b), which was wound on a smaller diameter tube, exhibited a better sensitivity. The results of the measurements are shown in FIGS. 5(a) and (b), with the spectra of FIG. 5(a) associated with the coil of FIG. 4(a) and the spectra of FIG. 5(b) associated with the coil of FIG. 4(b). The displacement of the spectrum caused by the refractive index variation is evident as a local shift and deformation of the spectrum. Referring to FIG. 5(a), the region outlined by a rectangle and enlarged to the right-hand side of the plot illustrates the dip that experienced the largest shift, shown as about 0.49 nm. From the known difference between the refractive indices of the two solutions (0.006), the sensitivity of this coil was estimated to be about 80 nm/RIU. A similar analysis, when performed on the plot of FIG. 5(b), yields a sensitivity of about 160 mm/RIU (with a refractive index difference being 0.003).

As mentioned above, evanescent coiled optical sensors of the present invention may be formed from either standard optical fiber or optical microfiber. FIGS. 6(a) and (b) illustrate transmission spectra of coils formed of optical microfiber wound on relatively small diameter silica rods. FIG. 6(a) is a 5× enlargement of an exemplary coil formed with an optical microfiber having a 5 micron radius, wound on a silica rod with a 0.55 mm radius and FIG. 6(b) is a 100× enlargement of an exemplary coil formed with an optical microfiber having a 0.45 micron radius and wound on a similar silica rod.

Various modifications can be utilized with the coiled evanescent optical sensor to further improve its sensitivity. For example, using relatively thin fibers (or microfibers), as well as tapered and/or coiled input and output couplers, will significantly reduce insertion losses in the system. Optimization of the input and output connections, which may also function as mode converters between the fundamental mode and other created modes, can allow for excitation of interfering WGMs, which generate larger sensitivity. The sensitivity of the coiled sensor will also increase with decreasing diameter of both the fiber forming the coil and the coil itself.

While the present invention has been particularly described and shown with reference to particular embodiments, it should be understood by those skilled in the art that various changes in form and detail may be made thereto without departing from the spirit and scope of the present invention as defined by the claims appended hereto.

What is claimed is:

1. An evanescent optical sensor for analyzing predetermined parameters of an ambient environment, the evanescent optical sensor comprising:
    an optical fiber coil formed to exhibit a coil radius R, a coil length L and comprising optical fiber having a predetermined radius r, the optical fiber coil defined as having an input and an output;
    an input optical mode converter disposed at an entrance of the optical fiber coil for splitting a propagating optical signal into a plurality of modes, the plurality of modes thereafter propagating along the optical fiber coil such that the optical fiber coil functions as a multiple-arm interferometer with each mode propagating as a different arm of the interferometer and affected differently by the ambient environment; and
    an optical spectrum analyzing arrangement coupled to the optical fiber coil output for receiving an interference output signal and analyzing predetermined parameters of the associated ambient environment based on the interference output signal.

2. An evanescent optical sensor as defined in claim 1, further comprising an output optical mode converter disposed between the optical fiber coil output and the optical spectrum analyzing arrangement for capturing the propagating plurality of modes as an interference output signal and then converting the plurality of modes into an optical output signal.

3. An evanescent optical sensor as defined in claim 2 wherein the output optical mode converter comprises an adiabatic mode converter.

4. An evanescent optical sensor as defined in claim 3 wherein the output optical adiabatic mode converter comprises a section of tapered optical fiber.

5. An evanescent optical sensor as defined in claim 1 wherein the optical fiber coil comprises a coil of standard single mode fiber.

6. An evanescent optical sensor as defined in claim 1 wherein the optical fiber coil comprises a coil of optical fiber having a diameter on the order of ten to one hundred microns.

7. An evanescent optical sensor as defined in claim 1 wherein the optical fiber coil comprises a coil of optical microfiber.

8. An evanescent optical sensor as defined in claim 1 wherein the analyzed predetermined parameters are selected from the group consisting of: temperature, pressure, sound and refractive index.

9. An evanescent optical sensor as defined in claim 1 wherein the input optical mode converter comprises an adiabatic mode converter.

10. An evanescent optical sensor as defined in claim 9 wherein input optical adiabatic mode converter comprises a section of tapered optical fiber.

11. An evanescent coupler sensor as defined in claim 1 wherein the optical coil creates whispering gallery modes as the plurality of propagating modes.

12. A method of sensing environmental changes in an ambient medium, the method comprising
    immersing an optical coil in an ambient medium to be analyzed;
    coupling an optical signal into an entrance of the optical coil through an input mode converter for introducing a plurality of modes into the optical coil;
    propagating the plurality of modes through the optical coil immersed in the ambient medium such that the optical fiber coil functions as a multiple-arm interferometer with each mode propagating as a different arm and affected differently by the ambient medium;
    analyzing a transmission spectrum associated with interference between the plurality of modes propagating along the multiple arms at an exit of the optical coil to sense the presence of environmental changes in the ambient medium.

13. The method as defined in claim 12 wherein the optical coil comprises a coil of optical fiber.

14. The method as defined in claim 12 wherein the optical coil comprises a coil of optical microfiber.

15. The method as defined in claim 12, further comprising propagating the plurality of modes as an interference output signal through an output mode converter at the exit of the optical coil.

16. The method as defined in claim 12 wherein the optical coil creates a plurality of whispering gallery propagating modes which thereafter propagate as separate signals along multiple arms of the interferometer.

* * * * *